(12) United States Patent
Elidan et al.

(10) Patent No.: US 11,024,428 B2
(45) Date of Patent: Jun. 1, 2021

(54) AUTOMATED METHOD AND SYSTEM FOR SCREENING AND PREVENTION OF UNNECESSARY MEDICAL PROCEDURES

(71) Applicant: SERENUS AI LTD., Tel Aviv (IL)

(72) Inventors: Josef Elidan, Tel Aviv (IL); Dan Berachowitz, Haifa (IL); Orly Elidan-Harel, Hod Hasharon (IL)

(73) Assignee: SERENUS AI LTD., Tel Aviv (IL)

( * ) Notice: Subject to any disclaimer, the term of this patent is extended or adjusted under 35 U.S.C. 154(b) by 488 days.

(21) Appl. No.: 15/776,205

(22) PCT Filed: Nov. 16, 2016

(86) PCT No.: PCT/IB2016/056880
§ 371 (c)(1),
(2) Date: May 15, 2018

(87) PCT Pub. No.: WO2017/093836
PCT Pub. Date: Jun. 8, 2017

(65) Prior Publication Data
US 2019/0333638 A1 Oct. 31, 2019

Related U.S. Application Data

(60) Provisional application No. 62/255,568, filed on Nov. 16, 2015.

(51) Int. Cl.
*G16H 50/30* (2018.01)
*G16H 20/40* (2018.01)

(52) U.S. Cl.
CPC .......... *G16H 50/30* (2018.01); *G16H 20/40* (2018.01)

(58) Field of Classification Search
CPC ........ G06Q 50/22; G06Q 50/02; G06Q 50/24; G16H 10/20; G16H 10/60; G16H 20/40;
(Continued)

(56) References Cited

U.S. PATENT DOCUMENTS 6,353,817 B1 3/2002 Jacobs et al.
6,584,445 B2 6/2003 Papageorge
(Continued)

FOREIGN PATENT DOCUMENTS

CN 1398376 A 2/2003
WO 0150330 A1 7/2001
(Continued)

OTHER PUBLICATIONS

Bughin et al., Artificial Intelligence: The Next Digital Frontier?, Jun. 2017, McKinsey Global Institute, pp. 1-80 (Year: 2017).*
(Continued)

*Primary Examiner* — Joy Chng
(74) *Attorney, Agent, or Firm* — Manelli Selter PLLC; Edward Stemberger

(57) ABSTRACT

An automated method for screening and preventing unnecessary medical/surgical procedures, comprising: retrieving medical/surgical procedures data from external and internal sources; computerizing a dynamic questioner with complex relations between questions and answers and a different impact for each answer in the context of the specific scenario and procedure by using experts input, latest research, statistics and machine learning modules; receiving from a user a request to provide a recommendation for a given medical/surgical procedure; providing a customized dynamic questionnaire to said user; computing a relative indication according to said answer's relative importance and impact on the decision to conduct said medical/surgical procedure; and generating a specific output for said user based on said medical/surgical procedure and the relative impact, including a relative indication for said medical/surgical procedure.

21 Claims, 16 Drawing Sheets

(58) Field of Classification Search
CPC ........ G16H 50/20; G16H 50/30; G16H 15/00; G06F 19/3418
USPC .......................................................... 705/2–3
See application file for complete search history.

(56) References Cited

U.S. PATENT DOCUMENTS

| | | | |
|---|---|---|---|
| 8,321,372 | B1 | 11/2012 | Rakshit et al. |
| 8,566,115 | B2 | 10/2013 | Moore |
| 8,635,183 | B1 | 1/2014 | Rakshit et al. |
| 2002/0035486 | A1* | 3/2002 | Huyn ...................... G16H 40/67 705/3 |
| 2003/0046113 | A1 | 3/2003 | Johnson et al. |
| 2003/0101076 | A1 | 5/2003 | Zaleski |
| 2010/0234691 | A1 | 9/2010 | Iwano et al. |
| 2011/0112848 | A1 | 5/2011 | Beraja et al. |
| 2013/0073306 | A1* | 3/2013 | Shlain .................... G16H 10/20 705/2 |
| 2015/0193583 | A1* | 7/2015 | McNair .................. G16H 50/20 705/2 |
| 2015/0282796 | A1 | 10/2015 | Nawana et al. |
| 2016/0232328 | A1* | 8/2016 | Sklar ...................... G16H 10/20 |

FOREIGN PATENT DOCUMENTS

| | | | | |
|---|---|---|---|---|
| WO | WO-2015066495 | A1 * | 5/2015 | ............. G16H 50/20 |
| WO | WO-2017121784 | A1 * | 7/2017 | ........... G06Q 10/101 |

OTHER PUBLICATIONS

WebMD Symptoms, downloaded Nov. 12, 2018, from http://symptoms.webmd.com/#introView.

* cited by examiner

Question 186

| | |
|---|---|
| AUTOMATIC | |
| TITLE FOR DOCTOR | What is the patient's age? |
| TITLE FOR PATIENT | What is your age? |
| TYPE | Select |
| JUSTIFICATION | Justification |
| PRIORITY | 40000 |
| REQUIRED KEY | Add a tag |
| MIN SCORE | 0 |
| MAX SCORE | 0 |
| VAS MIN SCORE | 0 |
| VAS MAX SCORE | 0 |
| DELETE | 0 |
| COPY EXISTING ANSWERS | Select set of answers |

FIG. 3

ANSWER 1

| | |
|---|---|
| TITLE | 0-12 years |
| JUSTIFICATION | Justification |
| WEIGHT | 0 |
| KEY | 0-12 x      add a tag |
| AUTO KEYS | add a tag |
| PRIORITY | 0 |
| END TEST ON THIS ANSWER | |
| KEYS FOR END TEST | add a tag |
| END TEST TEXT | End test text |
| FORCE SCORE | 0 |
| DELETE | 0 |

FIG. 4

OTORHINOLARYNGOLOGY > TONSILLECTOMY > QUESTIONS

➢ Show Questions | Hide Questions

New Question

SCORE

| From | To | Title |
|---|---|---|
| -4000 | -3001 | Further information is needed |
| -3000 | -2001 | Conservative treatment trial is needed. |
| -2000 | -1001 | General health contraindication. |
| -1000 | -401 | Further evaluation is needed. |
| -400 | 50 | There is no indication for the surgery, subject to a doctor's decision. |
| 51 | 58 | Equivocal result. Further consultation is needed. |
| 59 | 70 | Surgery is indicated (low level indication), subject to a doctor's decision. |
| 71 | 80 | Surgery indicated (medium level indication), subject to a doctor's decision. |
| 81 | 500 | Surgery indicated (high level indication), subject to a doctor's decision. |

FIG. 5

0 Edit 186 0        40000 0 0 0 0

What is the patient's age?
Title for Patient: What is your age?

Answers:

| Title | Weight | Tag | End_test | Force_score | Keys_for_end_test | Keys_for_auto_answer |
|---|---|---|---|---|---|---|
| 0-12 years | 0 | 0-12 | 0 | 0 | | |
| 13-30 years | 0 | 13-30 | 0 | 0 | | |
| 31-50 years | 0 | 31-50 | 0 | 0 | | |
| 51-70 years | 0 | 51-70 | 0 | 0 | | |
| 71-80 years | -5 | 71-80 | 0 | 0 | | |
| Above 80 years | -10 | Above 80 | 0 | 0 | | |

1 Edit 187 0        40000 0 0 0 0

How is the patient's general health?
Title for Patient: How is your general health?

Answers:

| Title | Weight | Tag | End_test | Force_score | Keys_for_end_test | Keys_for_auto_answer |
|---|---|---|---|---|---|---|

FIG. 7A

3 Edit 17 ⦁  How often has the patient suffered from recurrent tonsillitis?  29900  Recurrent 0 0 0 0
Title for Patient: How often did you suffered from recurrent tonsillitis?  tonsillitis Answers:

| Title | Weight | Tag | End_test | Force_score | Keys_for_end_test | Keys_for_auto_answer |
|---|---|---|---|---|---|---|
| 7 or more times per year For 1 year | 48 | | 0 | 0 | | |
| 5 or more times per year For 2 year | 48 | | 0 | 0 | | |
| 3 or more times per year For 3 year | 48 | | 0 | 0 | | |
| More than the above | 52 | | 0 | 0 | | |
| Less than the above | 30 | | 0 | 0 | | |
| Unknown | 10 | | 0 | 0 | | |

FIG. 7B

10 Edit 34 0     29250     Recurrent 0 0 4 -3
tonsillitis

What was the patient's quality of life during the tonsillitis event?
Title for Patient: What was your quality of life during the tonsillitis event?

Answers:

| Title | Weight | Tag | End_test | Force_score | Keys_for_end_test | Keys_for_auto_answer |
|---|---|---|---|---|---|---|
| Unknown | 0 | 0 | 0 | 0 | | |

11 Edit 270 0     29215     Recurrent 0 0 0 0
tonsillitis

Does the patient's suffer from antibiotics/allergy intolerance?
Title for Patient:

Answers:

| Title | Weight | Tag | End_test | Force_score | Keys_for_end_test | Keys_for_auto_answer |
|---|---|---|---|---|---|---|
| Yes | 0 | Antibiotics allergy | 0 | 0 | | |
| No | 0 | 13-30 | 0 | 0 | | |
| Unknown | 0 | 31-50 | 0 | 0 | | |

FIG. 7C

How many times has the patient been diagnosed with peritonsillar abscess by an ENT doctor?    29100    Peritonsillar abscess 0 0 0 0
Title for Patient: How many times were you diagnosed with peritonsillar abscess by an ENT doctor?

Answers:

| Title | Weight | Tag | End_test | Force_score | Keys_for_end_test | Keys_for_auto_answer |
|---|---|---|---|---|---|---|
| One Event | 20 | One event | 0 | 0 | | |
| Two Events | 60 | More than One event | 0 | 0 | | |
| More than two events | 75 | More than One event | 0 | 0 | | |
| Unknown | 0 | | 0 | 0 | | |

FIG. 7D

37 Edit 50 0  Has the patient been examined in a sleep laboratory?  11400  Snoring and 0 0 0 0
Title for Patient: Have you been examined in a sleep laboratory?  Sleep Apnea Answers:

| Title | Weight | Tag | End_test | Force_score | Keys_for_end_test | Keys_for_auto_answer |
|---|---|---|---|---|---|---|
| Yes | 0 | did sleep laboratory | 0 | 0 | | |
| No | 0 | Did not do sleep laboratory | 0 | 0 | | |
| Unknown | 0 | | 1 | -3500 | No Tonsillitis. No abscess | |

FIG. 7E

40 Edit 196 1     Title for Patient: Less than 12 years old with stops of breathing. Did not do sleep laboratory?     11325    did not do sleep laboratory    0 0 0 0

Answers:

| Title | Weight | Tag | End_test | Force_score | Keys_for_end_test | Keys_for_auto_answer |
|---|---|---|---|---|---|---|
| Yes stops of breathing | 30 | did sleep laboratory | 0 | | | Did not do sleep laboratory. O-12.yes stops of breathing |
| Usually stops of breathing | 30 | Did not do sleep laboratory | 0 | 0 | | Did not do sleep laboratory. O-12.Usually stops of breathing |
| Sometimes stops of breathing | 30 | | 0 | 0 | | Did not do sleep laboratory. O-12.Sometimes stops of breathing |

FIG. 7F

45 Edit 194  1

Title for Patient: Did not try conservative measures    11050  no conservative measures    0 0 0 0 0

Answers:

| Title | Weight | Tag | End_test | Force_score | Keys_for_end_test | Keys_for_auto_answer |
|---|---|---|---|---|---|---|
| 0-50 | -5 | | 0 | 0 | | 0-12, 13-30, 31-50 |
| 51-70 | -10 | | 0 | 0 | | 51-70 |
| 71-80 | -40 | | 0 | 0 | | 71-80 |
| Above 80 | -70 | | 0 | 0 | | Above 80 |

FIG. 7G

Has the operation been approved by a Hematologist?
Title for Patient: Has the operation been approved by a Hematologist?

6800   Blood   51   0   0   0
coagulation
problem

Answers:

| Title | Weight | Tag | End_test | Force_score | Keys_for_end_test | Keys_for_auto_answer |
|---|---|---|---|---|---|---|
| Yes | 0 | | 0 | 0 | | |
| No | 0 | | 1 | -600 | | |
| Unknown | 0 | | 1 | -3500 | | |

FIG. 7H

MEDecide ™ Report

TONSILLECTOMY

OTORHINOLARYNGOLOGY / TAKEN 10/03/2016 16:16

\* RESULTS
SURGERY IS INDICATED (HIGH LEVEL INDICATION), SUBJECT TO DOCTOR'S DECISION

QUESTIONS & ANSWERS

1. What is the patient's age?
0-12 years

2. How is the patient's general health?
VAS-1

3. Has the patient suffered from recurrent tonsillitis (infections of your tonsils)?
Yes 4. How often has the patient suffered from recurrent tonsillitis?
5 or more times per year, for 2 years 5. Have the patient's tonsillitis events been diagnosed by a physician?
Often 6. Have the patient's tonsillitis events been accompanied by fever?
Usually 7. Have the patient's tonsillitis events been accompanied by pus (white spots) on the tonsils?
Often 8. Have the patient's tonsillitis events been accompanied by positive culture for strept group A?
Sometimes

FIG. 8A

9. Have the patient's tonsillitis events been accompanied by enlarged and/or sensitive cervical lymph nodes?
Rarely 10. Have the patient's tonsillitis events been accompanied by abnormal blood tests (ESR, AST, CRP, WBC)?
Unknown 11. What was the patient's quality of life during the tonsillitis event?
VAS - 5

12. Has the patient suffered from peritonsillar abscess?

No

13. Has the patient suffered from snoring?
Yes

14. How strong is the patient's snoring?

Strong in all positions

15. Is the patient's snoring accompanied by stops of breathing?

Sometimes

16. What is the size of the patient's tonsils?

Large

17. Is the patient tired and sleepy during the day time?

Sometimes

18. Is the patient's work associated with a risk?
Not working

19 Has the patient been examined in a sleep laboratory?

Yes

20. What was the result of the sleep laboratory examination?
No obstructive sleep apnea syndrome was found 21. There are indications for tonsillectomy. No obstructive sleep apnea syndrome was

FIG. 8B

AUTOMATED METHOD AND SYSTEM FOR SCREENING AND PREVENTION OF UNNECESSARY MEDICAL PROCEDURES

FIELD OF THE INVENTION

The present invention relates to the field of medical systems with the purpose of providing a recommendation to medical professionals and/or patients in order to prevent unnecessary medical/surgical procedures.

CROSS-REFERENCE TO RELATED PATENT APPLICATIONS

This patent application claims priority from and is related to U.S. Provisional Patent Application Ser. No. 62/255,568, filed 16 Nov. 2015, this U.S. Provisional Patent Applications incorporated by reference in its entirety herein.

BACKGROUND

Symptom checker systems are known, such as: http://symptoms.webmd.com/#introView.

Second opinion service providers are available.

General health information providers are available; see e.g. sites/applications/forums/social network.

General diagnostics tools are known see e.g. IBM Watson

Patent documents describing the state of the art in relevant fields include: CN 1398376; USSN 20020184050 to Papageorge; USSN 20030046113 to Johnson, USSN 20030101076 to Zaleski, 20150282796 to Nawana; and U.S. Pat. No. 6,584,445 to Papageorge, U.S. Pat. No. 8,321,372 to Rakshit, et al., U.S. Pat. No. 8,566,115 to Moore, U.S. Pat. No. 8,635,183 to Rakshit, et al. and U.S. Pat. No. 6,353,817 to Jacobs, et al.

Millions of medical and surgical procedures are performed each year worldwide. The majority of these procedures are vital to the health and wellbeing of patients. However, recent studies demonstrate that an alarming percentage of the procedures are not justified and expose patients to unnecessary risks, hospitalization and financial expenses due to wrongful medical judgment. In view of the significant complication and even death rates of surgical procedures it is suggested that additional precautions should be established.

SUMMARY

Certain embodiments seek to provide an automated method and system assisting professionals and patients with their medical decision making process before going under medical/surgical procedures.

As opposed to general diagnostic tools, the invention focuses on filtering unnecessary medical/surgical procedures—preventing patients from facing unnecessary procedures with risks while saving valuable resources for medical institutions.

Certain embodiments seek inter alia to provide an advanced online tool configured for assisting patients' decision-making process when contemplating a medical/surgical procedure. The tool typically includes a logic base derived from experience of human experts, statistical information and analysis e.g. meta-analysis of published studies and machine learning modules. The tool is typically optimized on occasion, periodically or continuously.

Certain embodiments seek to provide a set-up stage in which questions and answers are setup in advance in a hierarchical flow in complex relations; each answer may then be assigned a different weight by human experts and/or may then be generated automatically using a manual or computerized procedure for learning new research and statistics.

The hierarchical flow and weights (impact) may be organized in any suitable logical relationship or structural combination. Different questions and answers and different weights may be assigned for the same answers in different combinations e.g. so as to yield a specific output for each individual end-user.

Certain embodiments seek to receive, from end-users, ex post facto (after the procedure) "reviews" (satisfaction questioners) including answers elicited regarding whether the procedure changed the end-user's life for worse/for better, does he feel better, and so forth.

Certain embodiments seek to provide a decision support system for patient end users facing medical/surgical procedures.

Certain embodiments seek to provide medical institutions with an advanced expert system before and after medical/surgical procedures.

Certain embodiments seek to provide insurance entities with an advanced filtering tool before and after medical procedures.

According to a first aspect of the invention there is provided an automated method of screening and preventing unnecessary medical/surgical procedures, comprising: retrieving medical/surgical procedures data from external and internal sources and storing the retrieved data; computerizing a set of dynamic questions and possible answers in a hierarchic data structure with complex relations and a different impact/weight for each answer in the context of each procedure and scenario, the weights calculated by analyzing, using an artificial intelligence module, the medical/surgical procedures data; receiving from a user a request to provide a recommendation for a given medical/surgical procedure; providing a customized dynamic questionnaire to the user, the questionnaire dynamically created according to the medical/surgical procedure and the weights assigned to the user's answers to previous questions in the questionnaire; computing a relative indication including providing a positive impact if a specific answer supports the medical/surgical procedure, and a negative impact if a specific answer negates the medical/surgical procedure according to the answer's relative importance and impact on a decision to conduct the medical/surgical procedure; and generating a specific output for the user based on the medical/surgical procedure and including a relative indication for the medical/surgical procedure.

The artificial intelligence module may comprise a logic base derived from experience of human experts, statistical information and analysis of published studies and machine learning modules. The method may further comprise assigning at least one key (tag) to the user's answer.

Dynamically creating the questionnaire may comprise selecting a next question according to keys accumulated so far in the questionnaire.

Dynamically creating the questionnaire may comprise ending the questionnaire according to keys accumulated so far in the questionnaire.

The user may be a patient and the specific output may comprise a report comprising at least one of: data related to the medical procedure, statistics, risks and questions to ask their physicians before going under the medical procedure.

The user may be a medical professional and the specific output may comprise at least one of: data on at least some of procedures, statistics, risks and other factors with regards to medical procedures decision making process in the daily practice.

According to a second aspect of the invention there is provided a computerized system for screening and preventing unnecessary medical/surgical procedures, comprising: a system server configured to: communicate with structured and unstructured external medical sources; store medical information from the external medical sources in a database; analyze the medical information using Natural Language Processing (NLP) and artificial intelligence tools; and use the analysis to communicate bi-directionally with users seeking recommendations for specific medical/surgical procedures, the communication comprising dynamic questionnaires; the system server may comprise a data mining and NLP module; a machine learning module; an Application Program Interface (API) module configured to enable data retrieval from various external medical sources; a reports and statistics module configured to generate personal reports to user following a question and answer session and to provide statistics calculated from a plurality of reports; a management and control module; at least one database; a web application configured to provide users with an interactive platform for communicating with the system; and a processing engine.

The data mining and NLP module may be configured to extract data from the external medical sources and transform it into an understandable structure for further use.

The extracted data may comprise data from patients' medical files.

The extracted data may be used for automatic labeling, for training the machine learning module.

The machine learning module may be configured to: calibrate the weight (impact) of each variable relevant to each medical procedure, by analyzing a large number of scenarios; and calibrate the system using at least one of: information mined from real medical files; patients' feedback after having undergone a medical procedure; and scanning latest researches, statistics and publications by health organizations.

The at least one database may comprise: patients' personal and medical information; reports generated by the reports and statistics module; a set of specific questions and possible answers for each medical/surgical procedure with complex relations, which are generated in advance e.g. by human experts and/or by machine learning modules; and a set of weights associated with each answer for different scenarios.

The questions and possible answers may be generated and updated by the system for each procedure, based on the data mining and NLP module and the machine learning module.

The weights may be generated and updated by the system for each procedure, based on the data mining and NLP module and the machine learning module.

The communicating with the system may comprise presenting queries, receiving answers and receiving reports and recommendations.

The processing engine may be configured to: select and present one question at a time to the user; receive an answer to the question; assign a current weight to the user's response; optionally assign a tag (key) to the user's response; select next question based on the user's response and one or more of the optional tags assigned to the user for previous answers; and provide results to the reports and statistics module.

The at least one database may comprise, for each medical/surgical procedure: a set of result range objects (RRO); and a multi-dimensional tree of question nodes (QN) and answer objects (AO) for each question node.

The RRO may comprise sone or more parameters selected from the group consisting of: procedure ID, Minimum Range Value (MINRV), Maximum Range Value (MAXRV), result text and result description.

The QN may comprise one or more parameters selected from the group consisting of: question text, question priority, required keys for unlocking the question, indication whether the question has an automatic answer, min and max Visual Analog Scale (VAS) range, min score to show question; max score to show question and a set of answer objects (AO).

The AO may comprise one or more parameters selected from the group consisting of: answer text, answer weight, answer key, automatic keys to choose answer, force score to assign to user and indication of test end.

BRIEF DESCRIPTION OF THE DRAWINGS

For better understanding of the invention and to show how the same may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 3 shows an exemplary structure of a question node;

FIG. 4 shows an exemplary structure of an answer object;

FIG. 5 shows an exemplary score table for a tonsillectomy procedure;

FIGS. 7A-7H provide an example of questions, possible responses and responses scoring, for a single procedure; and FIGS. 8A-8B are exemplary reports provided by the system to the user at the end of a session.

DETAILED DESCRIPTION OF CERTAIN EMBODIMENTS

Figure 1:
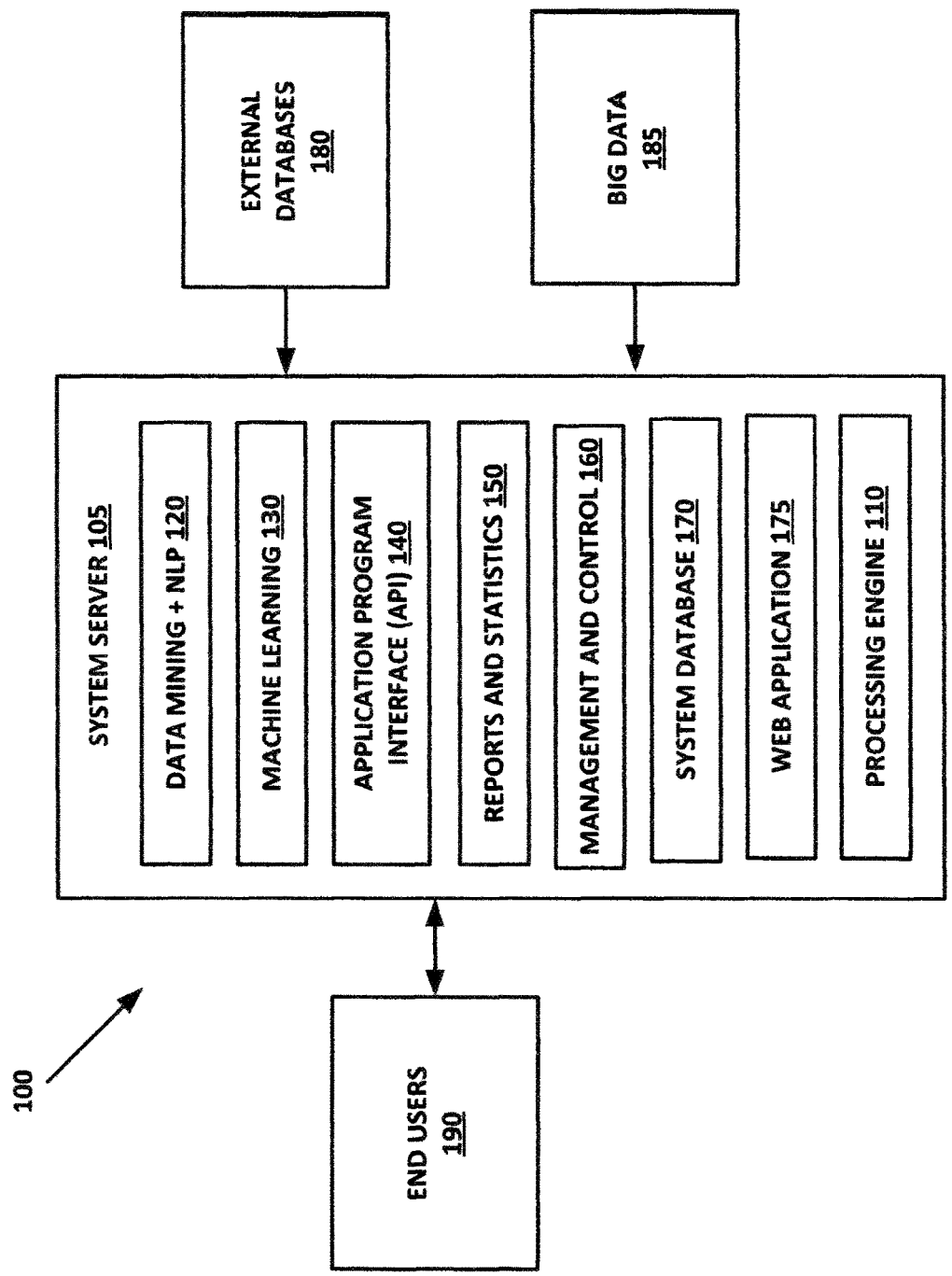
FIG. 1 is a schematic block diagram of the system according to embodiments of the present invention.

An automated artificial intelligence tool is provided, which provides assistance to professionals and patients facing a medical procedure (e.g. surgery) with their medical decision-making process. The tool may replicate the decision-making process of physicians, based on the knowledge of human experts, as well as machine learning techniques and the most recent research in each field. The tool is typically constantly reviewed and updated, using machine learning techniques, based on one or more of: professionals and users' feedback, patients' databases and research and a large number of medical records. As opposed to general diagnostic tools, the invention focuses on filtering unnecessary medical procedures—preventing patients from facing unnecessary procedures with risks while saving valuable resources for medical institutions.

The system operates as an expert system, with the following steps:

Step 1: Setting an Expert Baseline

While human experts lack the ability of a computer to track a huge number of weights and examples, they are however often quite effective in setting in place a small number of rules or weights that result in reasonably effective predictive systems. Setting up such a baseline is important from two complementing perspectives. First, learning models without an acceptable baseline can create the illusion of dramatic progress when in fact that absolute quality of the learned model is small. Second, and equally important, a hand-built system can aid in user-based data acquisition (see below).

Step 2: Simulated Expert Labels

Humans are particularly good at making great predictions in their area of expertise, even if they can't always break their decision into quantifiable elements. Thus, a natural first step for any learning system, particularly when acquisition of data is difficult or costly, is the use of simulated examples (=medical records), followed by expert labeling (=diagnosis). These can then be fed into a range of learning tools from various regression models to decision trees, and evaluated against the hand-coded system. Typically, this stage leads to first insights into basic strengths and weaknesses of the system, and serves as a guiding tool for subsequent data collection and algorithmic development. In particular, using active learning techniques, we can automatically define the scope of samples needed to improve the model quality, and substantially speed up further progress.

Step 3: Real Data

With a solid expert system and a learned improvement in place, the obvious next step is to use real-world data to continuously improve the system using advanced learning machinery by allowing for a greater breadth of measurements, "big data" scale of data processing using advanced machine learning techniques such as random forests or deep learning. At the high level, at the context of MEDecide™, three axis of data and ML progression should be pursued in parallel:

1. User-Based Records. As noted above, one of the benefits of putting a reasonable baseline in place is that this model can be used to provide a useful (even if not perfect) service to users. By simply using the system, each user creates a real record, which can then be labeled by an expert relatively quickly. Further, user follow-up feedback can serve as a (noisy) automated labeling mechanism which can further improve the system, similar to user labeling of images in a personal photo album. The obvious benefit of this axis is the low-cost accumulation of real cases.
2. Unlabeled Medical Records. Medical records from the practices of MEDecide experts and/or from medical institutions can similarly be labeled by experts. This can allow learning techniques to be applied to much richer measurement spaces, taking into account a wealth of information that goes well beyond what can be captured by a hand-coded questionnaire. While ultimately of higher quality than (1), this axis of progress is naturally slower and should just be pursued in parallel. Importantly, error analysis of models learned as part of (1) can act as a guide for informed collection of records, speeding up this stage.
3. Labeled Medical Records. Many health and insurance institutions also have medical records that have been labeled by the treating doctor. The obvious benefit is the availability of a large number of labeled records. While the quality of the labels is likely to be lower than that of the best physician in the field, mixture of experts' machine learning techniques can be used to mitigate this problem (often surpassing the best expert). Ultimately this fully automated axis is likely to lead to the biggest progress, simply due to the high-volume of (reasonably) labeled examples.

The system operates on a number of levels:

1. Providing a second opinion regarding the indication or contraindication for a specific medical/surgical procedure.
2. Providing a detailed report detailing the relative impact (positive or negative) of each factor that contributed to the recommendation or any other recommendation before a contemplated medical procedure (e.g. additional tests or treatments).
3. Storing detailed medical information relating to the patient.
4. Performing statistical analyses and finding hidden correlations between variables of multiple patients by interfacing with large medical systems (big data) and acquiring large volumes of information to be processed by the system's machine learning modules.
5. Improving the accuracy of the system by using machine learning modules and by analyzing large number of patients' records (big data) and users feedback.
6. Adding new indications for medical/surgical procedures by using machine learning modules and by analyzing large number of patients records and users feedback.

The system is configured to be installed in, amongst others:

Medical institutions and HMOs, to be used as an assisting tool to physicians before performing a medical/surgical procedure;

Insurance companies, to be used as a filtering tool before and after authorizing a medical/surgical procedure;

Legal entities, as an assisting tool during medical related lawsuits;

A proprietary website, to be used by patients seeking second opinion for undergoing medical procedures recommended by their physician.

The platform herein typically computerizes the process of medical/surgical decision-making by replicating the weight which a human expert e.g. physician may give to each of a plurality of situational factors.

The system uses a number of novel technologies, including:

1. A dynamic algorithm for building a set of complex relations between questions and answers and giving a dynamic weight to each answer.
2. A machine learning system that determines and improves the weight/impact of each relevant factor for the procedure being considered.
3. A machine learning system that interfaces with medical files for the purpose of calibration, finding new indications and hidden correlations between data of a plurality of patients regarding the recommendations given for medical/surgical procedures and the patients subsequent feedback and improving the overall precision of the system.

FIG. 1 is a schematic block diagram of the system according to embodiments of the present invention.

System 100 comprises one or more system servers (only one shown) 105, preferably a web server, communicating over the Internet with external databases 180, such as medical institutions' databases comprising patients' files, with big data resources 185, including both structured and unstructured data and with end users' electronic communication means 190, such as medical institutions' systems and patients' computers and/or mobile electronic communication devices.

System server 105 comprises a processor and some or all of the following computerized modules:

A data mining and Natural Language Processing (NLP) module 120, configured to extract information from external databases 180 and transform it into an understandable structure for further use, using NLP techniques. Data extracted includes, for example, data from patients' medical files such as lab reports, free text notations etc. The extracted data is used for automatic labeling for training the machine learning module.

A machine learning module 130, configured to:
Calibrate the weight (impact) of each variable relevant to each medical procedure, by analyzing a large number of scenarios.
Calibrate the system using information mined from real medical files (Big Data).
Calibrate the system using patients' feedback after having undergone the medical procedure.
Calibrate the system by scanning latest researches, statistics and publications by health organizations (e.g. American Academy Guidelines, World Health Organization, American and European health organizations, etc.).

An Application Program Interface (API) module 140 configured to enable data retrieval from various external medical sources.

A reports and statistics module 150 configured to generate personal reports to user following a question and answer session and to provide statistics calculated from a plurality of reports.

A management and control module 160 configured to manage the system including managing fields, procedures, questions and possible answers, databases, scores spectrums, impacts of answers, export and import information for machine learning purposes, managing clients, managing a combination of procedures. Managing—adding, editing and removing records. The management system is role and permissions based and is constantly being updated and evolved.

One or more database 170, storing:
Patients' information including lab test results, anamnesis, patients' personal data such as demographic data and reports generated by the reports and statistics module 150;
A set of specific queries and possible answers for each medical/surgical procedure, which are generated in advance e.g. by human experts;
A set of weights associated with each answer, which are pre-determined according to general knowledge and continuously updated by the latest researches, statistics and guidelines of the American and European Academies, and by machine learning modules 130;

A web application 175, providing users with an interactive platform for communicating with the system over the Internet, including presenting queries, receiving answers and receiving reports and recommendations.

A processing engine 110, configured to:
Select and present one query at a time to the user;
Grade user's response according to currently associated weight;
Determine next query based on last response.
Provide results to reports and statistics module 150.

Typically, in a set-up phase, a set of specific questions and possible answers for each medical/surgical procedure are generated in advance e.g. by human experts.

The questions and answers are organized in a hierarchic flowchart in complex relations and each answer receives a different weight (impact) according to a specific scenario and procedure.

The hierarchical flow and weights (impacts) may be organized in any suitable logical relationship or structural combination. It is possible that each case shall receive different set of questions and answers and that different weights may be assigned to the same answers in different combinations e.g. so as to yield a specific output for each individual end-user.

As a result and during the process, each user views a personally customized dynamic questionnaire, according to the selected assigned medical/surgical procedure, and the user's answers.

At the end of the process, the weights received for all the answers are analyzed to provide the relevant output.

According to certain embodiments, a patient facing a particular medical procedure or a medical professional, is asked relevant questions regarding the patient's medical condition.

According to embodiment of the invention, some answers may be pulled automatically by the system from the patient's medical records using NLP techniques.

Each answer receives a certain impact value, according to the relative importance and impact (i.e.weight) on the decision to conduct the specific medical procedure (similar to what a trained, unbiased surgeon does unconsciously when he considers a medical/surgical procedure). If the answer negates the specific medical procedure, it receives a negative impact.

At the end of the process the system analyses the input and the patient and/or the medical specialists receives a result, with the relative indication or contraindication for the medical/surgical procedure and additional recommendations e.g. further tests and conservative treatments needed before undergoing the medical procedure.

Examples of results:
Low indication for the medical/surgical procedure.
Moderate indication for the medical/surgical procedure.
High indication for the medical/surgical procedure.
Equivocal results. A second opinion or further discussion is needed.
The medical/surgical procedure is not justified.
The process is terminated because some crucial information is missing.
The process is terminated because more evaluation (test) is needed.

Figure 2:
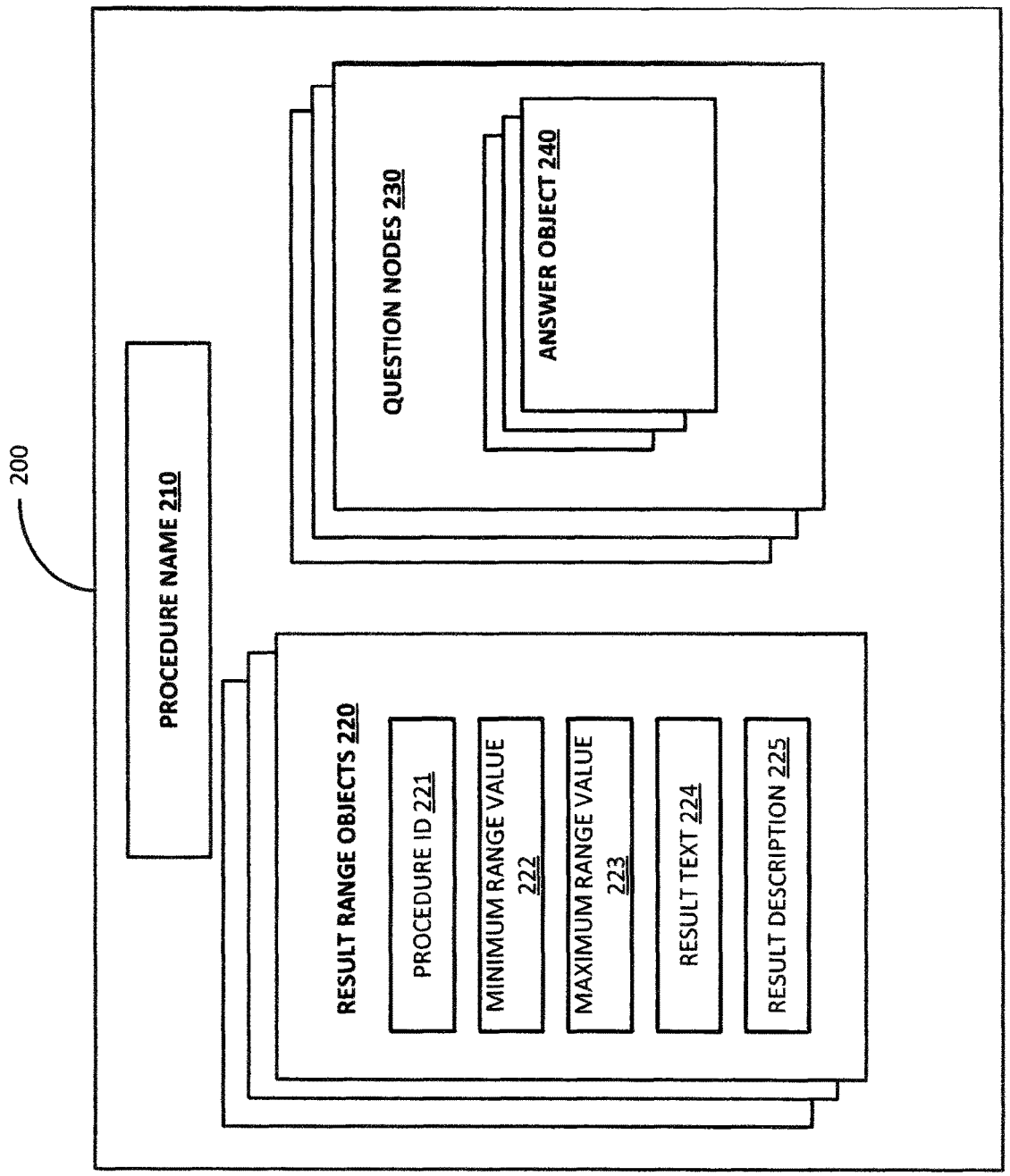
FIG. 2 is a schematic block diagram of an exemplary implementation of the structure of a single procedure entry in the system database.

FIG. 2 is a schematic block diagram of an exemplary implementation of the structure of a single procedure entry 200 in the system database 170.

A Procedure entry 200 may comprise some or all of the following objects:
Procedure name 210;
A set of result range objects (RRO) 220;
A multi-dimensional tree of question nodes (QN) 230 and answer object 240 for each question node.

A Result Range Object (RRO) 220 may for example comprise some or all of the following objects:

Procedure ID 221;
Minimum Range Value (MINRV) (number) 222;
Maximum Range Value (MAXRV) (number) 223;
Result Text 224;
Result Description 225.

A question node (QN) 230 may for example comprise some or all of the following objects:
Question text (text);
Question priority;
Required keys for unlocking the question (optional);
Indication whether the question has an automatic answer;
Visual Analog Scale (VAS) range (min and max);
Min score to show question;
Max score to show question;
A set of answer objects (AO).

An answer object (AO) 240 may for example comprise some or all of the following objects:
Answer text (text);
Answer weight (integer—positive or negative);
Answer key (AK) or any other indicator for automatically selecting the next question node.
Automatic keys to fire answer;
Force score to assign to user;
Indication of test end.

The keys serve for tracking selected ones of the user's answers and may change the course of the session by selecting the next question, determining whether the session should terminate and force a score.

The keys method may be replaced by any other method for automatically identifying which questions are relevant to a particular context, given a collection of possible questions that are relevant to a procedure.

Three components, together or independently, contribute to these methods:

1) An expert prior indicating the relevancy of a particular question given a particular response to another question.

2) An expert label that is generated as follows: questions are presented to the expert, either one after the other or as a complete scenario and the expert evaluates the relevancy of each question to the given context (either as a numerical score or a categorical one, e.g. "relevant", "not relevant").

3) Questions are identified as irrelevant based on statistical evaluation of relevancy to the target diagnosis task from past records.

The learning system may use either one or all of these components to learn a unified prediction system for the relevancy of a question in a particular context. This relevancy "score" will be used to automatically modify the structure of the questionnaire.

Another method that may replace keys:
Question tree—A data structure that is comprised of nodes or questions and answers nodes in which each question is a node and has a parent answer.

FIG. 3 shows an exemplary structure of a question node 230 for question no. 186.

The question node comprises interactive fields, which may be initially filled by a medical expert and later manually modified by a system administrator or automatically modified by the machine learning module 130.

The fields in the question node of FIG. 3 are:
Automatic—selection of the Automatic mode means that the question is an automatic question defined in the system and not presented to the system users. Automatic questions are actually "if—then" clauses that examine a set of tags (keys) assigned to the user during a session and determine a next course of action for the test accordingly.

Title for Doctor—the question text to be presented to a user who is a physician.
Title for patient—the question text to be presented to a user who is a patient.
Type—selection between a number of typed assigned by the system to the question. The selection is made according to the impact of the question on the sepcific procedure. Exemplary selection items are: main surgery factor, Critical examination, general health, etc.
Justification—free text.
Priority—priority assigned to the question. The priority influences the order of questions presented during a session.
Required key—keys (tags) that should have been assigned to the user during the current session in order to present this question.
Min score—the minimal score required to be accumulated during the current session in order to present this question.
Max score—the maximal score allowed to be accumulated during the current session in order to present this question.
VAS min score—a number to which a minimal score given in a Visual Analog Scale (VAS) answer should be transformed.
VAS max score—a number to which a maximal score given in a Visual Analog Scale (VAS) answer should be transformed.
Delete—selection of the Delete option means that the question is to be deleted from the system.
Copy existing answers—selection between answer sets to be copied from other questions.

FIG. 4 shows an exemplary structure of an answer object 240 for question no. 186 of FIG. 3.

The answer object comprises interactive fields, which may be initially filled by a medical expert and later manually modified by a system administrator or automatically modified by the machine learning module 130.

The fields in the answer object of FIG. 4 are:
Title the text selected by the user (optionally out of a plurality of selectable answers).
Justification—free text.
Weight—the weight (impact) assigned by the system to the current answer in the context of the procedure examined by the current session.
Key—the key (tag) assigned by the system to the current answer.
Auto keys—optional one or more keys defined by the system in order to assign an automatic answer to the question if the question is an automatic question.
Priority—priority assigned to the answer, meaning in which order the possible answers shall appear to the user.
End test on this answer—selection of this option causes the test to end if this answer was given.
Keys for end test—a set of keys having been assigned to the user during the current session that will cause the test to end
End test text—additional text to be displayed after the test ends.
Force score—system defined score to be assigned to a user having selected this answer, regardless of his previous score.
Delete—selection of the Delete option means that the answer is to be deleted from the system for the current question node, in the context of the current procedure.

FIG. 5 shows an exemplary score table for a tonsillectomy procedure.

Figure 6:
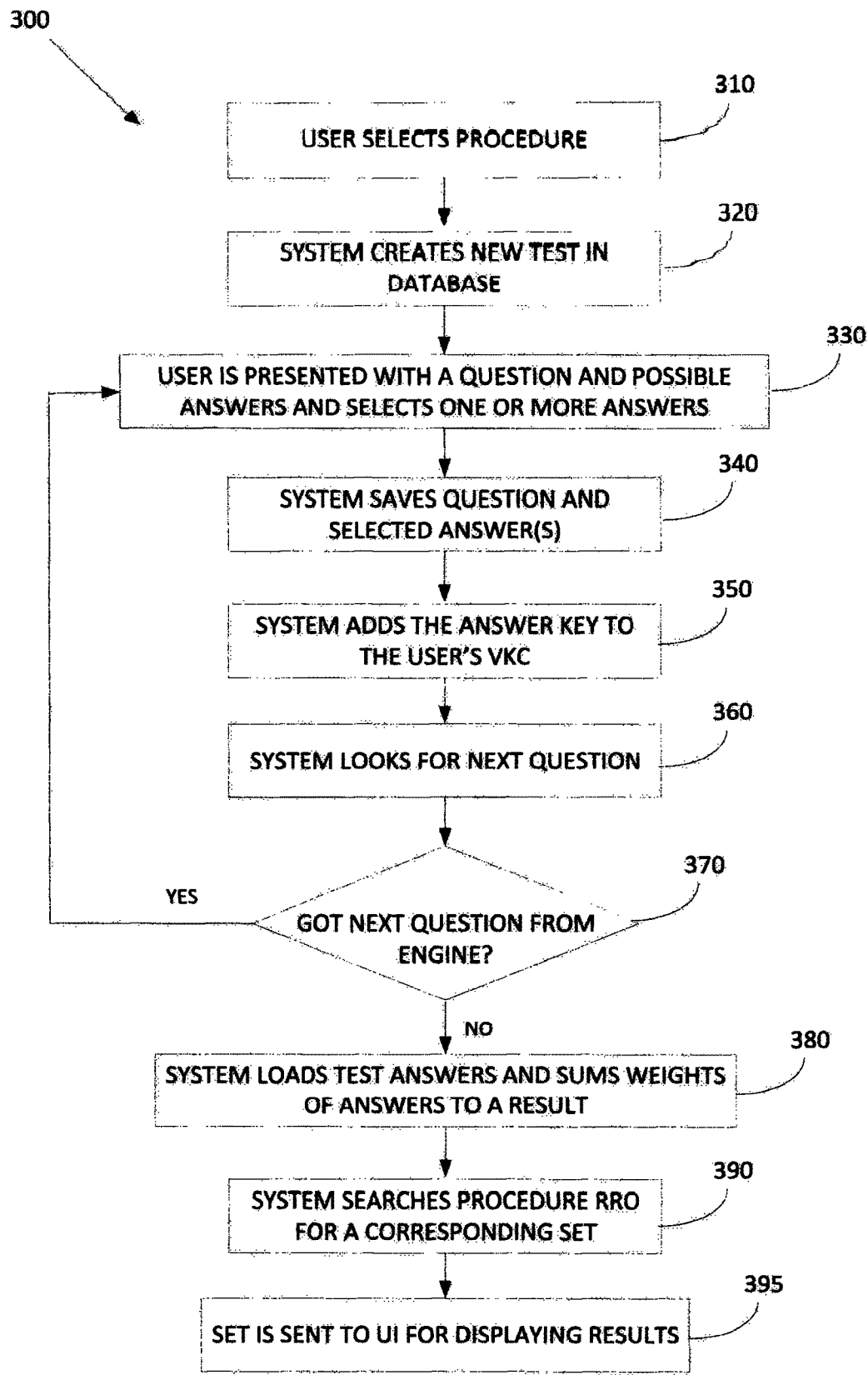
FIG. 6 is a flowchart showing the steps taken during an exemplary session initiated by a user for obtaining second opinion regarding a medical procedure.

FIG. 6 is a flowchart 300 showing the steps taken during an exemplary session initiated by a user for obtaining second opinion regarding a medical procedure.

In step 310 the user selects a procedure from a given list of procedures and clicks "start test". In step 320 a new test is created in the system database 170, which may be a proprietary data repository. The test may include a time-stamp, user info (IP etc.). A unique test ID is created.

During the test, the user typically sees the questions, ordered by their priorities. In step 330 the user is presented with a question and one or more possible answers to select from and selects the appropriate one or more answers.

The system then performs one or more of the following:
Saves the question and selected answer to a test database, with connection to the test ID (step 340).
Adds the answer key (AK) (if exists) to the user's virtual key-chain (VKC) which comprises all current test answer keys.

In step 360 the system checks in system's procedure's questions database for the next question that matches some or all of the following criteria:
A question with lower priority.
A question that can be unlocked using the user's current VKC (looping through all existing keys and matching with questions' required keys).

In step 370, if the system found a new question, it returns the new question object to the user interface and loops back to step 330.

If no new question was found, the system loads all the user's test answers from the database and sums the weight of the answers to a result (step 380).

In step 390 the system searches the procedure's RRO for the corresponding set, where result is between MINRV and MAXRV, and sends the found set to the user interface for results display (step 395).

FIGS. 7A-7H provide an example of the following, for a single procedure:
a. questions for presentation to an end user e.g. via his cellphone or personal computer, all or any subset of which may be presented;
b. possible multiple choice responses thereto;
c. scoring of each possible response;
all typically developed by a human expert such as a medical doctor and/or using machine learning modules, based on one or more of: professionals and users' feedback, patients' databases and research.

The example is of a single procedure (Tonsillectomy) within a single specialty; in practice hundreds of procedures, or more, may be supported, within plural specialties.

FIGS. 8A and 8B are exemplary reports provided by the system to the user at the end of a session.

The platform is typically configured to serve all or any subset of the following end-user types:
Patients considering a medical or a surgical procedure
Families and friends of patients considering a medical or a surgical procedure.
Professionals using this as a tool in their daily practice.
Medical institutions
Medical information providers
HMOs before approval of a certain surgical procedure
Insurance companies
Policy decision makers in the medical field.
Medical legal entities.
Advantages may include:
a. Unnecessary and risky surgical procedures shall be avoided.
b. Saving valuable resources for medical entities.
c. Improving the quality of medical treatment
d. Patients are provided with knowledge for optimized decision-making concerning health risks and life saving dilemmas.
e. Professionals and patients are facilitated in asking the right questions and trying alternative treatments and doing required test before going under risky medical procedures.
f. The decision-making process before medical procedure is improved, transparent and documented.

It is appreciated that the hierarchical flow and weights/points may be organized in any suitable logical relationship or structural combination. It is possible that different sets of questions and answers appear to each user and that different weights may be assigned for the same answers in different combinations e.g. so as to yield a specific output for each individual end-user.

For some surgical and/or other procedures, certain answers provided by an end-user may be deemed an absolute contraindication for the specific medical/surgical procedure and/or to the general/local anesthesia which are needed to conduct the procedure that was selected by the end-user, or may optionally result in the server presenting a recommendation for further information or examinations, another mode of treatment (e.g. conservative treatment) or another medical/surgical procedure entirely.

The tool can be presented in any digital platform and may provide end users with information on some or all of: procedures, descriptions, risks, statistics, tables, diagrams and drawings, along with automated decision making as described herein, thereby to enhance patients' ability to make more cautious medical decisions based on maximum information.

Features of the present invention, including method steps, which are described in the context of separate embodiments may also be provided in combination in a single embodiment. Conversely, features of the invention, which are described for brevity in the context of a single embodiment or in a certain order may be provided separately or in any suitable sub-combination or in a different order.

Any or all of computerized output devices or displays, processors, data storage and networks may be used as appropriate to implement any of the methods and apparatus shown and described herein.

The invention includes but is not limited to the embodiments recited in the following claims:

1. An automated method of screening and preventing unnecessary medical/surgical procedures, comprising:
retrieving medical/surgical procedures data from external and internal sources and storing said retrieved data;
computerizing a set of dynamic factors in a form of questions and possible answers in a hierarchic data structure with complex relations and a different dynamic impact/weight for each answer in the context of each procedure and scenario, said dynamic weights calculated by analyzing, using an artificial intelligence module, said medical/surgical procedures data;
receiving from a user a request to provide a recommendation for a given medical/surgical procedure;
providing a personalized customized dynamic questionnaire to said user, said questionnaire dynamically created, using said artificial intelligence module, according to said medical/surgical procedure, answers of said user, and said dynamic weights assigned to said user's answers to previous questions in said questionnaire;
computing a relative indication including providing a positive impact if a specific answer and its dynamic weight, supports said medical/surgical procedure, and a negative impact if a specific answer and its dynamic weight, negates the medical/surgical procedure according to said answer's relative importance and impact on a decision to conduct said medical/surgical procedure; and generating a specific personalized output for said user based on said medical/surgical procedure and including a relative indication for said medical/surgical procedure.

2. The method of claim 1, wherein said artificial intelligence module comprises a logic base derived from experience of human experts, statistical information and analysis of published studies and machine learning modules.

3. The method of claim 1, further comprising assigning at least one key (tag) to said user's answer.

4. The method of claim 3, wherein dynamically creating said questionnaire comprises selecting a next question according to keys accumulated so far in said questionnaire.

5. The method of claim 3, wherein dynamically creating said questionnaire comprises ending said questionnaire according to keys accumulated so far in said questionnaire.

6. The method of claim 1, wherein said user is a patient and wherein said specific output comprises a report comprising at least one of: data related to the medical procedure, statistics, risks and questions to ask their physicians before going under said medical procedure.

7. The method of claim 1, wherein said user is a medical professional and wherein said specific output comprises at least one of: data on at least some of procedures, statistics, risks and other factors with regards to medical procedures decision making process in the daily practice.

8. A computerized system for screening and preventing unnecessary medical/surgical procedures, comprising:
a system server configured to:
communicate with structured and unstructured external medical sources;
store medical information from said external medical sources in a database;
analyze said medical information using Natural Language Processing (NLP) and artificial intelligence tools; and
use said analysis to communicate bi-directionally with users seeking recommendations for specific medical/surgical procedures, said communication comprising dynamic questionnaires comprising dynamic questions, answers and said answers dynamic weights;
said system server comprising:
a data mining and NLP module;
a machine learning module;
an Application Program Interface (API) module configured to enable data retrieval from various external medical sources;
a reports and statistics module configured to generate personal reports to user following a question and answer session and to provide statistics calculated from a plurality of reports;
a management and control module;
at least one database;
a web application configured to provide users with an interactive platform for communicating with the system; and
a processing engine.

9. The system of claim 8, wherein said data mining and NLP module is configured to extract data from said external medical sources and transform it into an understandable structure for further use.

10. The system of claim 9, wherein said extracted data comprises data from patients' medical files.

11. The system of claim 9, wherein said extracted data is used for automatic labeling, for training the machine learning module.

12. The system of claim 8, wherein said machine learning module is configured to:
calibrate said dynamic weight (impact) of each variable relevant to each medical procedure, by analyzing a large number of scenarios; and
calibrate the system using at least one of:
information mined from real medical files;
patients' feedback after having undergone a medical procedure; and
scanning latest researches, statistics and publications by health organizations.

13. The system of claim 8, wherein said at least one database comprises:
patients' personal and medical information;
reports generated by the reports and statistics module;
a set of specific questions and possible answers for each medical/surgical procedure with complex relations, which are generated in advance by human experts and/or by machine learning modules; and
a set of dynamic weights associated with each answer for different scenarios.

14. The system of claim 13, wherein said questions and possible answers are generated and updated by the system for each procedure, based on said data mining and NLP module and said machine learning module.

15. The system of claim 13, wherein said dynamic weights are generated and updated by the system for each procedure, based on said data mining and NLP module and said machine learning module.

16. The system of claim 13, wherein said communicating with the system comprises presenting queries, receiving answers and receiving reports and recommendations.

17. The system of claim 13, wherein said processing engine is configured to:
select and present one question at a time to said user;
receive an answer to said question;
assign a current dynamic weight to said user's answer;
optionally assign a tag (key) to said user's answer;
select next question based on said user's answer and one or more of said optional tags assigned to said user for previous answers; and
provide results to said reports and statistics module.

18. The system of claim 13, wherein said at least one database comprises, for each medical/surgical procedure:
a set of result range objects (RRO); and
a multi-dimensional tree of question nodes (QN) and answer objects (AO) for each question node.

19. The system of claim 18, wherein said RRO comprise sone or more parameters selected from the group consisting of: procedure ID, Minimum Range Value (MINRV), Maximum Range Value (MAXRV), result text and result description.

20. The system of claim 18, wherein said QN comprises one or more parameters selected from the group consisting of: question text, question priority, required keys for unlocking the question, indication whether the question has an automatic answer, min and max Visual Analog Scale (VAS) range, min score to show question; max score to show question and a set of answer objects (AO).

21. The system of claim 18, wherein said AO comprises one or more parameters selected from the group consisting of: answer text, answer dynamic weight, answer key, automatic keys to choose answer, force score to assign to user and indication of test end.

\* \* \* \* \*